United States Patent [19]

Kingsley

[11] 4,029,761

[45] June 14, 1977

[54] METHOD FOR TREATING GINGIVITIS

[75] Inventor: Patrick John Kingsley, Barrow-on-Soar Loughborough, England

[73] Assignee: Fisons Limited, London, England

[22] Filed: Oct. 6, 1975

[21] Appl. No.: 619,822

[30] Foreign Application Priority Data

Oct. 19, 1974 United Kingdom ............. 45339/74

[52] U.S. Cl. .................................. 424/55; 424/283
[51] Int. Cl.$^2$ ................... A61K 31/35; A61K 7/24
[58] Field of Search ....................... 424/49, 55, 283

[56] References Cited
OTHER PUBLICATIONS

The Merck Manual, 12th ed., (1972) pp. 969–973.
Clinical Allergy, 1972 vol. 2, pp. 99–107.
The Lancet, April 1973, pp. 913–915.

*Primary Examiner*—Frederick E. Waddell
*Attorney, Agent, or Firm*—Merriam, Marshall, Shapiro & Klose

[57] ABSTRACT

There is described a method for the treatment of gingivitis (and particularly chronic gingivitis) which comprises administering an effective quantity of 1,3-bis(2-carboxychromon-5-yloxy)-2-hydroxypropane, or a pharmaceutically acceptable salt thereof, as active ingredient, to a patient suffering from gingivitis.

11 Claims, No Drawings

METHOD FOR TREATING GINGIVITIS

This invention relates to a new method.

According to our invention we provide a method for the treatment of gingivitis (and particularly chronic gingivitis) which comprises administering an effective quantity of 1,3-bis(2-carboxychromon-5-yloxy)-2-hydroxypropane, or a pharmaceutically acceptable salt thereof, as active ingredient, to a patient suffering from gingivitis.

Pharmaceutically acceptable salts which may be mentioned include the ammonium, alkali metal (e.g., sodium, potassium or lithium) and alkaline earth metal salts (e.g., calcium or magnesium), and salts with organic bases, e.g., salts with lower alkylamines such as methylamine or ethylamine, with substituted lower alkylamines, e.g., hydroxy substituted alkylamines or with simple monocyclic nitrogen heterocylic compounds, e.g., piperidine or morpholine. In particular the di-sodium salt (commonly known as cromolyn sodium or di-sodium cromoglycate) may be used.

The active ingredient may be administered on its own or in admixture with a suitable diluent or carrier. We prefer to use a composition containing the active ingredient, together with filters, detergents, abrasives etc. Thus there may be used a dentifrice composition containing from 0.1 to 5%, more preferably 0.5 to 2.5%, e.g. 2%, by weight of the active ingredient. The dentifrice composition may be presented in any convenient form, for example as a gel, solution, tooth paste or a tooth powder and may include a dentally acceptable abrasive, carrier, adjuvant or diluent, for example a detergent or flavouring.

Suitable dosages of the active ingredient are from about 1 to 100 mg, preferably about 5 to 25 mg and more preferably 10 to 15 mg per day which may be administered in divided doses from 1 to 4 times, and preferably twice, a day.

The active ingredient is preferably administered to the patient topically, e.g. by brushing or scrubbing onto the teeth, gums or oral mucous membrane. It is also preferred to use the active ingredient in finely divided form.

The active ingredient may be administered to the patient until the gingivitis is effectively controlled and thereafter as a prophylactic agent. A period of from about 2 to 6 weeks may be necessary to control the disease.

The invention is illustrated, but in no way limited by the following Example.

EXAMPLE

A female patient aged 40 years suffered from chronic gingivitis for 30 years. For most of this time she had swollen tender gums which bled and seeped every night leaving a smelly stain on her pillow in the morning, as well as bleeding easily on contact. Initially treatment consisted of applying, for 7–10 days every 6 months, dressings between the teeth that forced the gum swellings down. Later the interval was reduced to every four months, scrupulous dental care being maintained. 10 years ago a total gingivectomy was performed followed by cauterization 12 months later. Dental care continued every four months.

The patient was subsequently placed on a regime whereby she applied 7.5 mg of the disodium salt of 1,3-bis(2-carboxychromon-5-yloxy)-2-hydroxypropane morning and night in a toothpaste base. After 2 to 3 weeks the bleeding and seeping stopped, after 4 months her pillow was clean every morning, and although her gums were still slightly puffy, they were hardening with time and only bled when severely traumatised. After 12 months further treatment, the progress observed after 4 months had been maintained and further minor improvements of her condition were observed.

I claim:

1. A method for the treatment of gingivitis, which comprises topically administering onto the teeth, gums or oral mucous membrane an effective quantity of 1,3-bis(2-carboxychromo-5-yloxy)-2-hydroxypropane, or a pharmaceutically acceptable salt thereof, as active ingredient, to a patient suffering from gingivitis.

2. The method of claim 1, wherein the patient is suffering from chronic gingivitis.

3. The method of claim 1, wherein the active ingredient is the di-sodium salt of 1,3-bis(2-carboxychromon-5-yloxy)-2-hydroxypropane.

4. The method of claim 1, wherein the active ingredient is administered as a dentifrice composition containing from 0.1 to 5% by weight of active ingredient.

5. The method of claim 1, wherein from 1 to 100 mg of active ingredient are administered per day.

6. The method of claim 5, wherein from 5 to 25 mg of active ingredient are administered per day.

7. The method of claim 6, wherein from 10 to 15 mg of active ingredient are administered per day.

8. The method of claim 1, wherein the active ingredient is administered from 1 to 4 times a day.

9. The method of claim 8, wherein the active ingredient is administered twice a day.

10. The method of claim 1, wherein the active ingredient is administered topically to the teeth, gums or oral mucous membrane.

11. A method for the prophylatic treatment of gingivitis which comprises topically administering onto the teeth, gums or oral mucous membrane an effective quantity of 1,3-bis(2-carboxychromon-5-yloxy)-2-hydroxypropane, or a pharmaceutically acceptable salt thereof, to a pateint liable to suffer from gingivitis.

* * * * *